(12) United States Patent
DeLucia et al.

(10) Patent No.: US 7,045,029 B2
(45) Date of Patent: May 16, 2006

(54) STRUCTURED MATERIAL AND METHOD OF PRODUCING THE SAME

(75) Inventors: Mary Lucille DeLucia, Roswell, GA (US); Sandy Chi-Ching Tan, Roswell, GA (US); Eugenio Go Varona, Marietta, GA (US); Jessica B. King, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 531 days.

(21) Appl. No.: 09/871,118

(22) Filed: May 31, 2001

(65) Prior Publication Data

US 2003/0077970 A1   Apr. 24, 2003

(51) Int. Cl.
*B32B 31/14* (2006.01)

(52) U.S. Cl. ......................................... 156/85; 156/183

(58) Field of Classification Search ............ 156/84–85, 156/183, 250, 253, 256, 259, 167, 180–181; 264/282, 283; 428/373, 374, 152–154, 198, 428/316.6, 317.9; 442/394, 400, 401, 50, 442/51, 361, 362, 414, 398; 604/358, 365, 604/366, 367, 378, 385.01, 385.23; 162/111–113
See application file for complete search history.

(56) References Cited

U.S. PATENT DOCUMENTS

| | | | |
|---|---|---|---|
| 3,180,775 A * | 4/1965 | Sexsmith ...................... 156/85 |
| 3,214,323 A * | 10/1965 | Russell et al. .............. 428/198 |
| 3,272,898 A | 9/1966 | Knee |
| 3,338,992 A | 8/1967 | Kinney |
| 3,341,394 A | 9/1967 | Kinney |
| 3,441,021 A * | 4/1969 | Endres ........................ 602/43 |
| 3,502,763 A | 3/1970 | Hartmann |
| 3,542,615 A | 11/1970 | Dobo et al. |
| 3,546,056 A * | 12/1970 | Thomas ...................... 428/110 |
| 3,597,299 A * | 8/1971 | Thomas ...................... 428/108 |
| 3,692,618 A | 9/1972 | Dorschner et al. |
| 3,802,817 A | 4/1974 | Matsuki et al. |
| 3,849,241 A | 11/1974 | Butin et al. |
| 3,925,127 A * | 12/1975 | Yoshioka ..................... 428/101 |
| 4,133,924 A * | 1/1979 | Seino et al. ................. 428/164 |
| 4,340,563 A | 7/1982 | Appel et al. |
| 4,560,372 A | 12/1985 | Pieniak |
| 4,762,521 A | 8/1988 | Roessler et al. |

(Continued)

FOREIGN PATENT DOCUMENTS

DE    195 23 497 A 1    1/1997

(Continued)

OTHER PUBLICATIONS

A.A. Burgeni and C. Kapur, *Capillary Sorption Equilibria in Fiber Masses*, Textile Research Journal, vol. 37, May 1967, pp. 356-366.

*Primary Examiner*—Jessica Rossi
(74) *Attorney, Agent, or Firm*—Pauley Petersen & Erickson

(57) ABSTRACT

A method for producing a structured material for accommodating passage of fluids, particularly high viscosity fluids, through the structured material. In one embodiment, the structured material is a composite material formed of a first layer, for example a polypropylene polymer, having a first shrinkage extent and a second layer bonded to the first layer, for example an ethylene-propylene copolymer, having a second shrinkage extent different from the first shrinkage extent. In another embodiment, a structured heterogenous material is made of a heterogeneous mixture of at least two homogeneous fiber sets or components having different shrinkage extents.

12 Claims, 6 Drawing Sheets

U.S. PATENT DOCUMENTS

| | | |
|---|---|---|
| 4,842,596 A | 6/1989 | Kielpikowski et al. |
| 5,057,368 A | 10/1991 | Largman et al. |
| 5,069,970 A | 12/1991 | Largman et al. |
| 5,108,820 A | 4/1992 | Kaneko et al. |
| 5,108,827 A | 4/1992 | Gessner |
| 5,171,239 A | 12/1992 | Igaue et al. |
| 5,207,664 A | 5/1993 | Blanco |
| 5,257,982 A | 11/1993 | Cohen et al. |
| 5,272,236 A | 12/1993 | Lai et al. |
| 5,277,976 A | 1/1994 | Hogle et al. |
| 5,294,482 A | 3/1994 | Gessner |
| 5,322,728 A | 6/1994 | Davey et al. |
| 5,336,552 A | 8/1994 | Strack et al. |
| 5,466,410 A | 11/1995 | Hills |
| 5,482,772 A | 1/1996 | Strack et al. |
| 5,491,016 A * | 2/1996 | Kaiser et al. ............... 428/198 |
| 5,536,555 A | 7/1996 | Zelazoski et al. |
| 5,567,501 A * | 10/1996 | Srinivasan et al. ......... 428/137 |
| 5,571,619 A | 11/1996 | McAlpin et al. |
| 5,643,240 A | 7/1997 | Jackson et al. |
| 5,679,042 A | 10/1997 | Varona |
| 5,707,468 A | 1/1998 | Arnold et al. |
| 5,789,328 A * | 8/1998 | Kurihara et al. ............ 442/387 |
| 5,804,021 A | 9/1998 | Abuto et al. |
| 5,814,178 A * | 9/1998 | Jacobs ........................ 156/290 |
| 5,830,555 A | 11/1998 | Srinivasan et al. |
| 5,840,633 A * | 11/1998 | Kurihara et al. ............ 442/200 |
| 5,851,935 A | 12/1998 | Srinivasan et al. |
| 5,873,868 A | 2/1999 | Nakahata |
| 5,883,028 A | 3/1999 | Morman et al. |
| 5,906,879 A | 5/1999 | Huntoon et al. |
| 5,914,184 A | 6/1999 | Morman |
| 5,990,377 A | 11/1999 | Chen et al. |
| 6,001,303 A | 12/1999 | Haynes et al. |
| 6,018,093 A | 1/2000 | Roe et al. |
| 6,217,889 B1 * | 4/2001 | Lorenzi et al. ............. 424/401 |
| 6,491,777 B1 * | 12/2002 | Bevins et al. ............... 156/167 |
| 6,491,928 B1 * | 12/2002 | Smith, III .................... 424/401 |

FOREIGN PATENT DOCUMENTS

| | | | |
|---|---|---|---|
| EP | 0687757 | * | 12/1995 |
| EP | 0 586 924 | | 10/1997 |
| EP | 0 617 940 | | 11/1999 |
| GB | 2 284 786 A | | 6/1995 |
| JP | 06031869 | | 2/1994 |
| JP | 08176947 | | 7/1996 |
| WO | WO 93/09741 | * | 5/1993 |

* cited by examiner

STRUCTURED MATERIAL AND METHOD OF PRODUCING THE SAME

BACKGROUND OF THE INVENTION

1. Field of the Invention

This invention relates to a method for producing a structured material, for example a cover material or topsheet for personal care absorbent articles including diapers, feminine pads, incontinence garments, training pants, wound care products, and the like. The structured material according to this invention provides a structure for accommodating passage of fluids, particularly high viscosity fluids such as menses, runny bowel movements, wound exudate and blood, therethrough.

2. Description of Related Art

Personal care absorbent articles such as sanitary napkins, disposable diapers, incontinent-care pads and the like are widely used, and much effort has been made to improve the effectiveness and functionalities of these articles. Conventional cover materials used in personal care absorbent articles do not provide for high viscosity fluids, for example menses, runny bowel movements, wound exudate and blood. As a result, the conventional cover materials used in personal care absorbent articles leak and contribute to poor skin health. Many conventional liners absorb water from the high viscosity fluids. However, these conventional liners do not provide for particle intake. As a result, the particles contained within the high viscosity fluids separate during absorption of the water and tend to remain on the surface of the liner to produce undesired interactions with the wearer's skin.

Many conventional intake liners used in personal care absorbent articles such as feminine pads and diaper products require holes to provide appropriate performance. Two valuable properties for good performance are intake rate and rewet value. Currently, there are several model materials which provide adequate performance. However, these materials are costly to manufacture.

Accordingly, there is a need for a method or process for providing an improved cover material which effectively manages high viscosity fluids such as menses, runny bowel movements, wound exudates and blood.

There is also a need for a method or process for producing a cost-effective cover material having intake and rewet properties at parity with or superior to more expensive model cover materials.

SUMMARY OF THE INVENTION

Materials suitable as a cover material or intake liner for feminine care products must quickly and efficiently handle menses. Menses has an average viscosity of approximately 10 cP. This is a slightly higher viscosity than the viscosity of water, which is about 1.0 cP. The cover material should have a fast intake rate for very viscous fluids, prevent menses from flowing back to the surface (reduce rewet), and allow only minimal staining. An ideal cover material may have the performance of a film (clean and dry) with the clothlike feel of spunbond.

Materials suitable for use as a cover material or intake liner for infant care, including diapers and training pants, must quickly and efficiently handle runny bowel movements without compromising the management of other fluids such as urine. A runny bowel movement has an average viscosity of about 25 Poise and a range of about 0.1 Poise to about 110 Poise. Approximately, 87% of a runny bowel movement is water and the remaining 13% is composed of particles. The particles range in size from about 5.0 microns to about 900 microns with an average size of about 100 microns. Desirably, the cover material has a pore radius of greater than about 200 microns, more desirably greater than about 600 microns, to pass bowel movement particles through the cover material. It is also desirable to enhance pore size and pore volume to increase web permeability thereby increasing the fluid intake rate. The cover material should also have a single point acquisition (direct intake and localization of runny bowel movements), high z-directional flow, rapid dewatering, and surface flow resistance.

The high viscosity fluid needs for professional health care, including bandages and the like, are slightly different than those for feminine care and infant care. The main priority for the development of fenestration products is to produce cost-effective alternatives for the current foam pads. The fenestration products should have a cover material with a high coefficient of friction to prevent the surgical tools from slipping on the fenestration reinforcement, and an ability to absorb wound exudates and other surgical fluids.

Accordingly, it is one object of this invention to provide a process for making a structured material for use as a cover material in a personal care absorbent article for managing high viscosity fluids, for example menses, runny bowel movements, wound exudates and blood without compromising the management of other fluids, for example urine.

It is another object of this invention to provide a process for making a structured material for a personal care absorbent article which is soft and comfortable, absorbent, clean and dry.

It is another object of this invention to provide a process for producing a structured material which has fluid intake and rewet properties similar to or better than more expensive model materials.

These and other objects of this invention are addressed by providing a continuous process for producing a structured material having a structure suitable for use in a personal care absorbent article for managing high viscosity fluids. The structured material may be a structured composite material having at least two layers of unique polymer composition or a structured heterogenous material having a heterogeneous mixture of at least two homogenous fiber sets with unique polymer composition.

Desirably, the second layer or fiber set is made from a polymer or polymer blend different from the polymer or polymer blend of the first layer or fiber set to promote the differential shrinkage. Thus, the second layer or fiber set has a shrinkage extent, at constant temperature, different than the shrinkage extent of the first layer or fiber set. The polymers selected for the second layer or fiber set and the polymers selected for the first layer or fiber set have sufficiently different propensities to shrink over a range of temperatures, and desirably, have different orientation, crystallization, solidification and/or elastic properties. In one embodiment of this invention, a similar polymer or polymer blend is selected for the first layer or fiber set and the second layer or fiber set, having a different crystallization and/or orientation to produce different shrinkage extents.

The structure of the structured material is produced or formed by the differential shrinkage. The shrinkable second layer or fiber set is made of a polymer or polymer blend which may or may not have a shrinking point lower than the shrinking point of the polymer or polymer blend of the first layer or fiber set. For example, the second layer or fiber set is made of an ethylene-propylene copolymer and the first layer or fiber set is made of a propylene polymer. The material is heated to a temperature corresponding to at least the shrinking point of the second layer or fiber set, causing the second layer or fiber set to shrink. This shrinkage of the second layer or fiber set results in bunching or puckering of the first layer or fiber set, thus forming or creating the structure. Because this differential shrinkage may be a latent process, the differential shrinkage process may be induced during the fabrication of the structured material or it may be delayed until the structured material is transferred to a converting machine or product manufacturing site. Further, it is apparent to those having ordinary skill in the art that the polymer or polymer blends used to produce the first layer or fiber set and the second layer or fiber set may be exploited so that the first layer or fiber set will shrink relative to the second layer or fiber set.

The structured material produced according to this invention is particularly useful for management of high viscosity fluids, for example menses, runny bowel movement, wound exudate and blood, and may be used as an intake liner or a cost-effective replacement for surge materials. The structured material exhibits fluid intake rates and low rewet values similar to or better than more expensive model cover materials.

Definitions

As used herein, the term "film" refers to a thermoplastic film made using a film extrusion and/or forming process, such as a cast film or blown film extrusion process.

As used herein, the term "nonwoven fabric or web" means a web having a structure of individual fibers or threads which are interlaid, but not in an identifiable manner, as in a knitted fabric. Nonwoven fabrics or webs have been formed from many processes such as, for example, meltblowing processes, spunbonding processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91).

As used herein, the term "spunbond fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992 and U.S. Pat. No. 3,341,394 to Kinney, U.S. Pat. No. 3,502,763 to Hartmann, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns. The fibers may also have shapes such as those described in U.S. Pat. No. 5,277,976 to Hogle et al., U.S. Pat. No. 5,466,410 to Hills, and U.S. Pat. No. 5,069,970 and U.S. Pat. No. 5,057,368 to Largman et al., which describe hybrids with unconventional shapes.

The term "meltblown fibers" means fibers formed by extruding a molten thermoplastic material through a plurality of fine, usually circular, die capillaries as molten threads or filaments into converging high velocity gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin and in U.S. Pat. No. 6,001,303 to Haynes, et al. Meltblown fibers are microfibers which may be continuous or discontinuous, are generally smaller than 10 microns in diameter, and are generally self bonding when deposited onto a collecting surface. Meltblown fibers used in the present invention are preferably substantially continuous in length.

As used herein, the term "polymer" generally includes, but is not limited to, homopolymers, copolymers, such as for example, block, graft, random and alternating copolymers, terpolymers, etc., and blends and modifications thereof. Further, unless otherwise specifically limited, the term "polymer" shall include all possible geometric configurations of the molecule. These configurations include, but are not limited to, isotactic, syndiotactic and random symmetries.

As used herein, the term "bicomponent fibers" refers to fibers which have been formed from at least two polymers extruded from separate extruders but spun together to form one fiber. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another or may be a side-by-side arrangement or an "islands-in-the-sea" arrangement. Bicomponent fibers are taught in U.S. Pat. No. 5,108,820 to Kaneko et al., U.S. Pat. No. 5,336,552 to Strack et al., and European Patent 0586924. For two component fibers, the polymers may be present in ratios of 75/25, 50/50, 25/75 or any other desired ratios.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, but rather typically form fibrils or protofibrils which start and end at random. Biconstituent fibers are sometimes also referred to as multiconstituent fibers. Fibers of this general type are taught, for example, by U.S. Pat. Nos. 5,108,827 and 5,294,482 to Gessner.

As used herein, the term "bonded carded web" refers to webs made from staple fibers which are sent through a combing or carding unit, which breaks apart and aligns the staple fibers in the machine direction to form a generally machine direction-oriented fibrous nonwoven web. Such fibers are usually purchased in bales which are placed in a picker which separates the fibers prior to the carding unit. Once the web is formed, it is then bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface, if so desired. Another suitable and well-known bonding method, particularly when using bicomponent staple fibers, is through-air bonding.

As used herein, the term "composite" or "composite material" refers to a material which is comprised of one or more layers of nonwoven fabric combined with one or more other fabric or film layers. The layers are usually selected for the different properties they will impart to the overall composite. The layers of such composite materials are usually secured together through the use of adhesives, entanglement or bonding with heat and/or pressure.

As used herein, the term "personal care product" or "personal care absorbent product" means feminine hygiene products, diapers, training pants, absorbent underpants, adult incontinence products, wipes, wound care products, including bandages, and the like.

As used herein, the term "shrinkage extent" refers to an amount of shrinkage of a fiber or a component when the fiber or component is activated to shrink, for example by applying or introducing heat to the fiber or component at a temperature greater than a shrinking temperature of the fiber or component or at least one of the fiber or components, if the fiber or a material comprises more than one component.

Fiber shrinkage extent and "percent shrinkage" may be measured using a simple test wherein fibers are extruded at several different draw pressures, for example at 0 psi, 7 psi and 14 psi. The extruded fibers are placed in an oven set at a constant temperature for a given period of time. For example, the fibers in accordance with this invention where placed in a Thermolyne 9000 oven set at a constant temperature of about 135° C. for a five minute period. The length of each fiber is measured before it is placed in the oven and after it has been heated in the oven for the given period of time. The fiber shrinkage extent or extent of shrinkage can be determined by subtracting the final fiber length from the initial fiber length. The percent shrinkage can be determined by subtracting the final fiber length from the initial fiber length, dividing by the initial fiber length and multiplying by 100. Referring to the above example, a fiber having an initial length of 10 inches and a final length of 8.0 inches will have a percent shrinkage of 20%.

$$\frac{(10.0 - 8.0)}{10.0} \times 100 = 20\% \qquad \text{Eq. (1)}$$

The percent shrinkage may be from about 0% to about 99%, depending upon fiber composition, fiber denier, and process conditions.

As used herein, the term "thermoplastic" describes a material that softens when exposed to heat and which substantially returns to a nonsoftened condition when cooled to room temperature.

As used herein, the term "z-direction" refers to fibers disposed outside of the plane of orientation of a web, such fibers having a z-direction component resulting from post-forming processing of a nonwoven web, such as differential shrinkage and/or creping the nonwoven web.

As used herein, the term "homogeneous component" refers to a component having uniform composition or structure.

These terms may be defined with additional language in the remaining portions of the specification.

DETAILED DESCRIPTION

Figure 1:
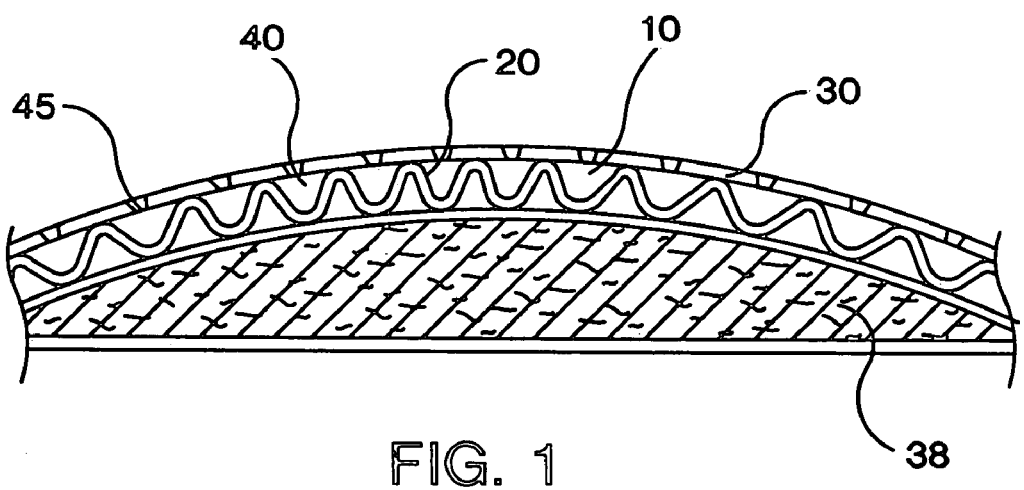
FIG. 1 is a sectional view of an exemplary personal care absorbent article having a structured composite material produced in accordance with one embodiment of this invention.

This invention relates to a structured material 10, for example a cover material or topsheet for use in a personal care absorbent article as shown in FIG. 1, which when utilized with an absorbent core 44, permits superior management of high viscosity fluids. Proper management of these high viscosity fluids for feminine care in particular requires good intake (absorbency), low staining (cleanliness), low rewet and low fluid retention (dryness). Accordingly, this invention provides a continuous method or process for producing a structured material 10 which has high permeability, significant fiber orientation in the z-direction (bulk) and good tactile properties for enhanced dryness.

In accordance with one embodiment of this invention, the continuous process produces a structured composite material 10 having a second layer 30, for example a film liner, applied and/or bonded to a first layer 20, for example a substrate. The second layer 30 subsequently shrinks relative to the first layer 20 to produce a structure 40 of the structured composite material 10. Such shrinkage process is referred to as "differential shrinkage." In accordance with another embodiment of this invention, the first layer 20 may shrink relative to the second layer 30, depending on the polymers or polymer blends chosen to form the first component or layer 20 and the second component or layer 30.

The process for producing the structured composite material 10 begins with forming the first layer 20. The first layer 20 may have more than one layer. The first layer 20 is formed or produced by any conventional means well known in the art. Desirably, the first layer 20 has an initial basis weight of about 0.2 osy to about 2.0 osy, more desirably about 0.3 osy to about 1.5 osy. The combined initial basis weight of the first layer 20 and the second layer 30 should be lower than the desired basis weight of the final product. The first layer 20 may be pleated, corrugated, thermoformed or embossed and desirably has a high modulus and high resiliency to maintain its structure during packaging and use.

Fibrous nonwoven webs work particularly well as base materials from which to form the first layer 20. The nonwoven web may be any type of thermoplastic nonwoven web. For instance, the nonwoven web may be a spunbond web, a meltblown web, a bonded carded web, or a combination including any of the above. Suitable base materials include spunbond-meltblown-spunbond laminates, coform, spunbond-film-spunbond laminates, bicomponent spunbond, bicomponent meltblown, biconstituent spunbond, biconstituent meltblown, pulp, superabsorbent, and combinations thereof.

A wide variety of thermoplastic polymer materials can be used to make the nonwoven web. Exemplary polymer materials include without limitation, polypropylene, polyethylene (high and low density), ethylene copolymers with $C_3$–$C_{20}$ α-olefins, propylene copolymers with ethylene or $C_4$–$C_{20}$α-olefins, butene copolymers with ethylene, propylene, or $C_5$–$C_{20}$ α-olefins, polyvinyl chloride, polyesters, polyamides, polyfluorocarbons, polyurethane, polystyrene, polyvinyl alcohol, polylactic acid, caprolactams, and cellulosic and acrylic resins. Bicomponent and biconstituent thermoplastic webs may also be utilized, as well as webs containing blends of one or more of the above-listed thermoplastic polymers.

Suitable polyolefins include, but are not limited to, polyethylene, polypropylene, polybutylene, and the like; suitable polyamides include, but are not limited to, nylon 6, nylon 6/6, nylon 10, nylon 12 and the like; and suitable polyesters include, but are not limited to, polyethylene terephthalate, polybutylene terephthalate and the like. Particularly suitable polymers for use in the present invention are polyolefins including polyethylene, for example, linear low density polyethylene, low density polyethylene, medium density polyethylene, high density polyethylene and blends thereof; polypropylene; polybutylene and copolymers as well as blends thereof. Additionally, the suitable fiber forming polymers may have thermoplastic elastomers blended therein. In addition, staple fibers may be employed in the nonwoven web as a binder.

After the first layer 20 is formed, a second layer 30, desirably a shrinkable second layer 30, is formed and applied or bonded to the first layer 20 to form a composite material. The second layer 30 may comprise more than one layer. The second layer 30 is desirably compliant, soft feeling, and non-irritating to a wearer's skin. Further, the second layer 30 can be less hydrophilic than an absorbent core positioned underneath the structured composite material 10, to present a relatively dry surface to the wearer and permit liquid to readily penetrate through its thickness. Desirably, the second layer 30 has a basis weight of about 0.3 osy to about 2.5 osy, more particularly about 0.44 osy to about 1.0 osy.

The second layer 30 may be placed or applied onto the first layer 20 by an appropriate technology considering the materials used to form the first layer 20 and the second layer 30. For example, the second layer 30 may be extruded or sprayed onto the first layer 20 in a desired pattern. For a smocked effect, parallel lines are appropriate. A variety of shapes and/or patterns other than parallel lines may be used. Alternatively, the second layer 30 may be a web or a film that is laminated or bonded to the first layer 20 using thermal bonding, adhesive bonding including pin bonding, differential speed bonding and/or other bonding techniques well known in the art. Thermal point bonding and adhesive spiral bonding are desired because these bonding methods do not damage the first layer 20.

Desirably, the second layer 30 is made from a polymer or polymer blend different from the polymer or polymer blend of the first layer 20 to promote the differential shrinkage of the layers 20, 30, as discussed below. Thus, the second layer 30 has a shrinkage extent, at constant temperature, different than the shrinkage extent of the first layer 20. In one embodiment of this invention, the polymers selected for the second layer 30 and the polymers selected for the first layer 20 have sufficiently different shrinking points, desirably having a shrinking point difference of at least about 10° C., and, desirably, have different orientation, crystallization, solidification and/or elastic properties. The difference in shrinking points between the selected polymers facilitates the differential shrinkage of the layers 20, 30 and the heat activated bonding process.

In one embodiment of this invention, a similar polymer or polymer blend is selected for the first layer 20 and the second layer 30, having a different crystallization and/or orientation to produce different shrinkage extents for the first layer 20 and the second layer 30. Further, the polymer or polymer blend may be treated, for example with additives and/or fillers to produce different shrinkage extents.

Suitable thermoplastic polymer materials for making the second layer 30 include those polymer materials listed above for making the first layer 20. Various woven and nonwoven fabrics can be used for the second layer 30. For example, the second layer 30 can be composed of a meltblown or spunbond web of polyolefin fibers. The second layer 30 can also be a bonded carded web composed of natural and/or synthetic fibers. The second layer 30 can be composed of a substantially hydrophobic material, and the hydrophobic material can, optionally, be treated with a surfactant or otherwise processed to impart a desired level of wettability and hydrophilicity. For example, the material can be surface treated with about 0.10 weight percent to about 0.50 weight percent, more desirably about 0.20 weight percent to about 0.40 weight percent of a surfactant commercially available from the Cognis Corp. of Ambler, Pa. and produced in Cincinnati, Ohio under the trade designation GLUCOPON. Other suitable surfactants can also be used. The surfactant can be applied by any conventional means, such as spraying, printing, brush coating or the like. The surfactant can be applied to the entire second layer 30 or can be selectively applied to particular sections of the second layer 30, such as the medial section along the longitudinal centerline.

Alternatively, the second layer 30 can be a film formed from any suitable film-forming thermoplastic polymer. Examples of suitable polymers include without limitation polyethylene, polypropylene, copolymers of mainly ethylene and $C_3$–$C_{12}$ alpha-olefins (commonly known as linear low density polyethylene), copolymers of mainly propylene with ethylene and/or $C_4$–$C_{12}$ alpha-olefins, and flexible polyolefins including propylene-based polymers having both atactic and isotactic propylene groups in the main polypropylene chain. Other suitable polymers include without limitation elastomers, for example polyurethanes, copolyether esters, polyamide polyether block copolymers, ethylene vinyl acetate copolymers, block copolymers having the general formula A-B-A' or A-B such as copoly (styrene/ethylene-butylene), styrene-poly (ethylene-propylene)-styrene, styrene-poly (ethylene-butylene)-styrene, polystyrene/poly(ethylene-butylene)/polystyrene, poly (styrene/ethylene-butylene/styrene), and the like. Metallocene-catalyzed polyolefins are also useful, including those described in U.S. Pat. Nos. 5,571,619; 5,322,728; and 5,272,236, the disclosures of which are incorporated herein by reference.

During or after the fabrication process, other optional steps may be included for completeness. For example, post fabrication treatments including surface treatments and UV and/or microwave treatments may be included as steps in the process of producing the structured material according to this invention.

In one embodiment of this invention, the second layer 30 is stretched in a machine direction before it is bonded to the first layer 20. The second layer 30 is pre-oriented using a machine direction orienter prior to bonding the second layer 30 to the first layer 20. Desirably, the second layer 30 is stretched from about 1.5 times to about 6.0 times its initial length, more desirably about 2.0 to about 4.0 times its initial length, still more desirably about 3.0 times its initial length.

After the second layer 30 is bonded, laminated or applied to the first layer 20, the structure 40 of the composite material is produced. In accordance with one embodiment of this invention, a structure 40, defined by the first layer 20 and the second layer 30, is produced or formed by differential shrinkage of the layers 20, 30. For example, the shrinkable second layer 30 is made of a polymer or polymer blend having a shrinking point lower than the shrinking point of the polymer or polymer blend of the first layer 20, such as an ethylene-propylene copolymer, and the first layer 20 is made of a propylene polymer. The composite material is heated to a temperature corresponding to at least the shrinking point of the second layer 30, shrinking the second layer 30. Desirably, but not necessarily, the composite material is heated to a temperature below the shrinking point of the first layer 20. In accordance with one embodiment of this invention, the first layer 20 may shrink as a result of heat application, however to a lesser extent than the second layer 30.

This differential shrinkage of the second layer 30 results in bunching or puckering of the first layer 20, thus forming or creating the structure 40 defined by the first layer 20 and the second layer 30. Because this differential shrinkage may be a latent process, the differential shrinkage may be induced during the fabrication of the structured composite material 10 or it may be delayed until the structured composite material 10 is transferred to a converting machine or product manufacturing site. Advantages to being able to produce the structure 40 at any time during the fabrication process include the ability to transport and handle a relatively flat composite material and the increased integrity of the structure 40, i.e. the structure 40 will not be damaged during transportation to the manufacturing site.

Figure 2:
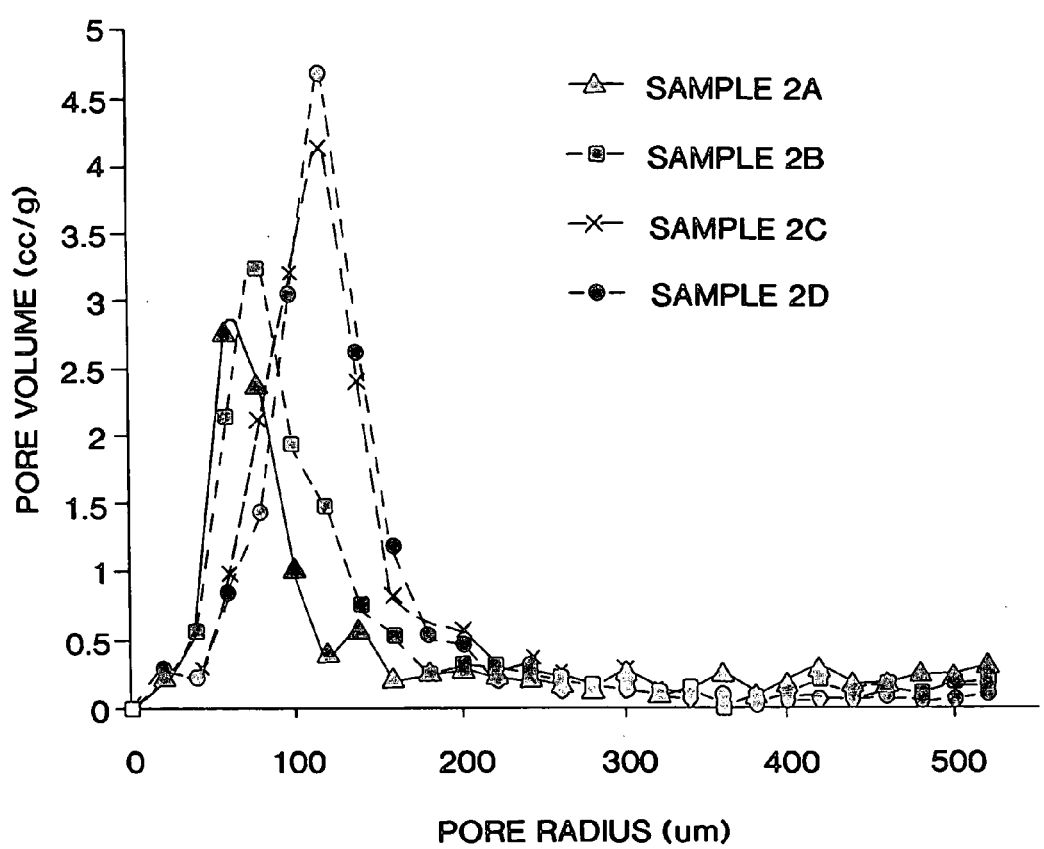
FIG. 2 is a pore radius distribution chart for a structured material produced in accordance with one embodiment of this invention.

The polymers or the polymer blends used to produce the first layer 20 and the second layer 30 can be chosen to exploit the differential shrinkage anticipated by the polymer properties. It is apparent to those having ordinary skill in the art that the polymers or polymer blends used to form the first layer 20 and the second layer 30 may be exploited to produce the first layer 20 which shrinks relative to the second layer 30. The structured composite material 10 produced by differential shrinkage of the fibers changes in density and porosity in response to the temperature profile during heat shrinkage. As shown in FIG. 2, differential shrinkage of the layers 20, 30 provides an increase in overall pore radius and pore volume to the structured composite material 10, which increases the bulk and decreases the overall density of the structured composite material 10. FIG. 2 is a pore radius distribution chart the data for which was obtained as discussed below in TEST METHODS. Samples of a structured composite material 10 made of a bilayer spunbond web having the first layer 20 made of a polypropylene polymer and the second layer 30 made of an ethylene-propylene random copolymer (3% by weight ethylene and 97% by weight propylene) were passed through a cure oven at a temperature between about 270° F. and about 290° F. at a rate of about 50 feet per minute (fpm) to about 250 fpm.

Figure 3:
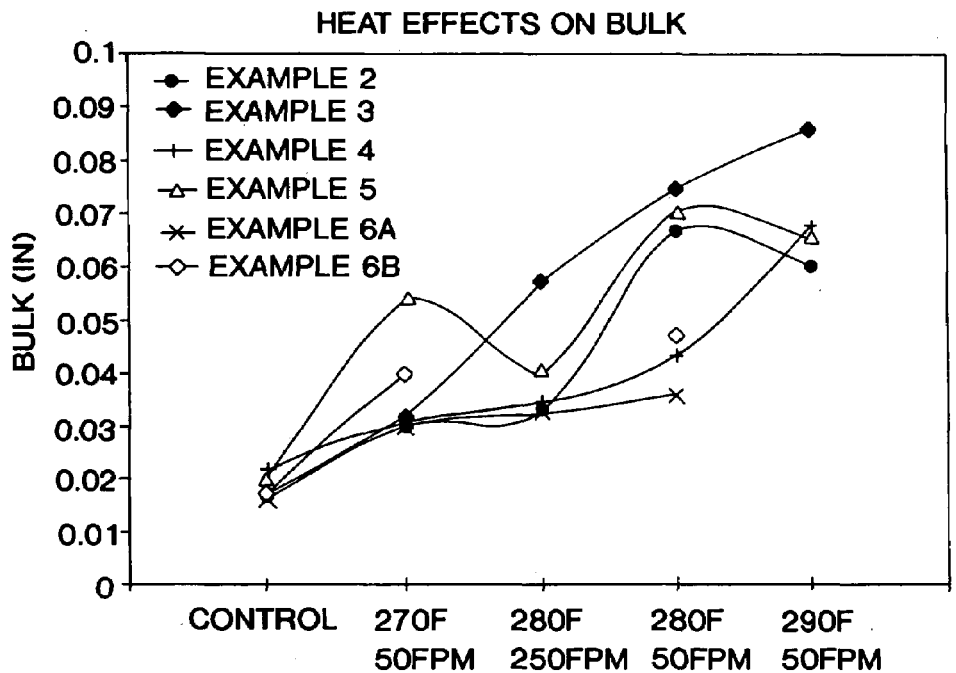
FIG. 3 shows the effects of heat during the differential shrinkage process on the bulkiness of a structured material in accordance with one embodiment of this invention.
Figure 4:
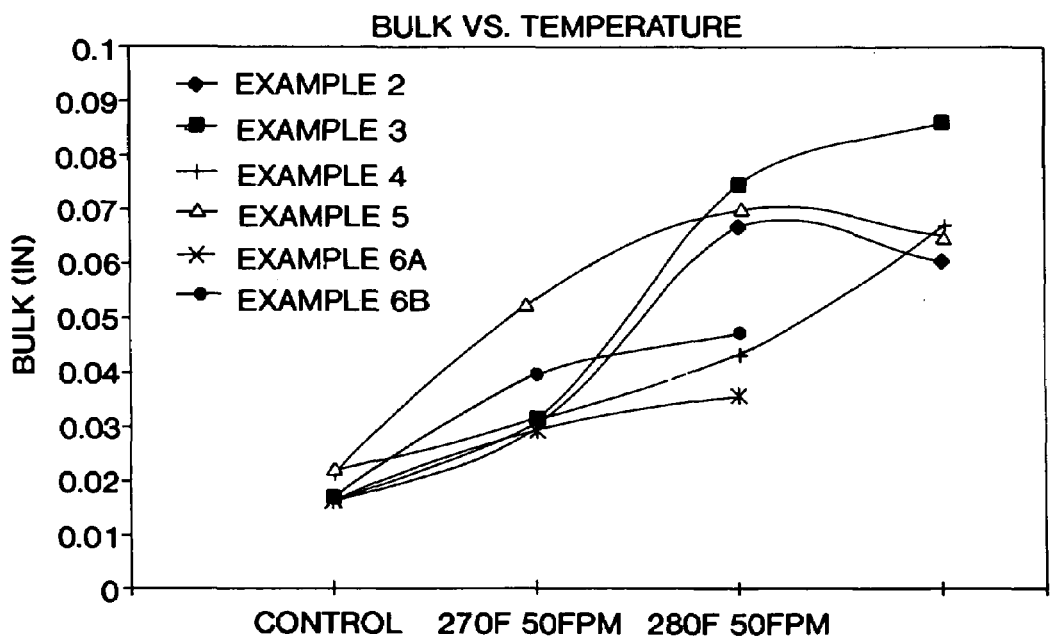
FIG. 4 shows the effects of heat during the differential shrinkage process on the bulkiness of a structured material in accordance with one embodiment of this invention.

FIGS. 3 and 4 show the heat effects on bulk for Examples 1 through 6 discussed below. As shown in FIGS. 3 and 4, the bulk and structure 40 of the composite material 10 generally increased as the temperature applied to the composite material during the differential shrinkage process increased. Further, the rate at which the composite material moves through the cure oven may effect the overall bulk and structure 40 of the composite material. The increased bulk and structure 40 of the composite material are a direct result of the differential shrinkage of the second layer 30, which causes the first layer 20 to bunch or pucker to produce the structure 40 of the composite material.

In one embodiment of this invention, a multiple layer structured composite material 10 having a pore size gradient in the z-direction is created by bonding at least one non-shrinkable first layer 20 to at least one shrinkable second layer 30. Desirably, the layers are bonded together at discrete points, as in thermal or adhesive point bonding, such that the layers are free to move at the non-bonded area. When the shrinkable second layer 30 is activated to shrink, the non-shrinkable first layers 20 move in a z-direction or in a plane generally perpendicular to the composite material to form fiber loops.

For example, in this embodiment a dual layer structured composite material 10 is produced having a non-shrinkable first layer 20 bonded to a shrinkable second layer 30. The structured composite material 10 forms a pore size gradient with large pores in the fiber loops of the non-shrinkable first layer 20 and smaller pores in the shrinkable second layer 30. The dual layer composite material may also be creped (with the shrinkable second layer 30 against the drum, as discussed below) before the second layer 30 is activated to shrink. This produces a stabilized creped structure 40 after shrinkage with low density, high permeability, and good resistance to tensile stresses. Suitable applications for the dual layer structured composite material 10 include, but are not limited to, high permeability dry liners, low flowback liners, and filtration media.

A multiple layer structured composite material 10 having two non-shrinkable first layers 20 and a shrinkable second layer 30 disposed between the two non-shrinkable first layers 20, may also be produced in accordance with this embodiment. The structured composite material 10 has a symmetrical structure 40 wherein each of the non-shrinkable first layers 20 form a large pore layer and the shrinkable second layer 30 forms a small pore layer. Suitable applications for the multiple layer structured composite material 10 made in accordance with this embodiment include, but are not limited to, wiping applications and filter media.

In accordance with one embodiment of this invention, a structured heterogenous material 10 is produced from a heterogeneous mixture of homogeneous fibers. Desirably, each homogeneous component or set of homogeneous fibers is composed of a different polymer, having a different shrinking point or temperature and a unique shrinkage extent. Alternatively, the first and second homogeneous components may be the same or similar polymer with different characteristics and/or properties. In accordance with one embodiment of this invention, the heterogeneous material is produced having a first homogeneous component having a first shrinkage extent and a second homogeneous component having a second shrinkage extent different from the first shrinkage extent. The first homogeneous component may have the same or similar shrinking point as the shrinking point of the second homogeneous component but may have a different shrinking extent than the second homogeneous component.

Suitable polymers and polymer blends used to produce the components of the structured heterogeneous material 10 include those used to produce the first layer 20 and/or the second layer 30 of the structured composite material 10. The polymers can be chosen to exploit the differential shrinkage anticipated by the polymer properties. The heterogeneous material changes in density and porosity in response to the temperature profile during differential shrinkage. Differential shrinkage of the homogeneous fibers provides an increase in overall pore radius and pore volume to the heterogenous material, increasing the bulk and structure 40 and lowering the overall density of the heterogeneous material.

For example, polyethylene-alpha olefin copolymer fibers (containing 20–99% by weight ethylene and 1–80% by weight alpha-olefin) and polypropylene polymer fibers can be melt spun to form the heterogeneous material having fiber sets of distinct polymer composition. The heterogeneous material desirably has an initial basis weight of about 0.2 osy to about 2.0 osy, more desirably about 0.3 osy to about 1.5 osy, still more desirably about 0.7 osy. Other suitable polymer combinations include, but are not limited to, other thermoplastic polymers with different shrinkage extents, for example polyesters, polyamides, other olefinic copolymers, biconstituents and blends thereof. Desirably, the heterogenous material has a bond area of about 1.0% to about 8.0%, more desirably about 5.0% to minimize land area and maximize fiber area.

A filler, for example calcium carbonate, diatomaceous earth, titanium dioxide, talc, or the like, may be added to at least one of the homogeneous components, for example the polypropylene polymer fibers, to impart an aesthetically pleasing hand to the heterogeneous material. The filler enhances the heat absorption properties of the polymers and thus increases the options for thermal initiation of shrinkage.

Heat is subsequently introduced to the heterogeneous material to produce the structure 40 of the heterogeneous material. The polyethylene copolymer fibers shrink at a lower shrinking temperature than the polypropylene polymer fibers. In accordance with one embodiment of this invention, heat may be introduced to the heterogeneous material at a temperature sufficient to shrink the polyethylene copolymer fibers but not the polypropylene polymer fibers. Alternatively, heat may be introduced to the heterogeneous material at a temperature sufficient to shrink the polyethylene copolymer fibers and the polypropylene polymer fibers, whereby the polyethylene copolymer fibers shrink to a greater extent than the polypropylene polymer fibers. Heat is introduced to the heterogeneous material by conventional means including, but not limited to, a hot air gun, a cure oven, a convection oven, an infrared-heater, microwave, radio frequency and a through-air bonder. For example, the heterogeneous material may be passed through a cure oven set at about 250° F. to about 300° F., desirably about 270° F. to about 290° F. at a rate of about 25 fpm to about 300 fpm, desirably about 50 fpm to about 250 fpm. The heat introduced to the heterogeneous material as it passes through the cure oven and at least the polyethylene copolymer fibers shrink.

As a result of the polyethylene copolymer shrinkage, the polypropylene polymer fibers bunch or pucker to produce the structure 40 of the heterogeneous material. Desirably, the heterogeneous material shrinks to about 0% to about 99% of its initial length, more desirably about 10% to about 70% of its initial length to produce a soft, structured heterogeneous material 10.

Experiments were run in which the heterogeneous material contained 50% by weight polypropylene fibers and 50% by weight fibers formed from an ethylene-propylene copolymer containing 3% by weight ethylene and 97% by weight propylene. As shown in Table 1, the introduction of heat to the heterogeneous material resulted in an increased basis weight and bulk, as well as an increase in the average permeability of the structured heterogeneous material 10. Further, the introduction of heat to the heterogeneous material resulted in a change in density of about 53%. As suggested in Table 1, the density of the structured heterogenous material 10 can be lowered significantly, depending on the change in thickness of the structured heterogeneous material 10. The reduction in density may be about 0% to about 95%, desirably about 40% to about 70%. In another embodiment of this invention, the density of the structured heterogenous material 10 may increase as a result of differential shrinkage. An outer layer, for example a film liner, may subsequently be applied and/or bonded to the structured heterogeneous material 10.

TABLE 1

| Polymer | Polypropylene/ Copolymer | Polypropylene/ Copolymer |
| --- | --- | --- |
| Conditions | as spun | treated at 275° F., 70 fpm |
| Basis weight (g/m$^2$) | 25 | 31 |
| Basis weight (osy) | 0.73 | 0.92 |
| Bulk (m) | 0.00044 | 0.0012 |
| Density (g/m$^3$) (Basis weight/Bulk) | 5.6E+04 | 2.6E+04 |
| Change in Density (%) | — | 53 |
| Average Permeability (Darcies) | 1350 | 2610 |

In another embodiment of this invention, the heterogeneous material is developed by melt spinning a plurality of fiber into a net or scrim material. At least one of the fibers and the scrim material has a shrinkable component. Suitable nets or scrim materials include, but are not limited to, commercially available nets including polypropylene, polyamide and polyester nets. Other suitable nets include oriented-heat set and non-oriented, pre-heat set polypropylene scrim hand samples supplied by CONWED; polypropylene, polyethylene, polyamide, and HYTREL nets supplied by Naltex; and nets having semi-elastic properties.

For example, copolymer fibers or fibers made of another shrinkable polymer can be spun into an olefin net or scrim material. The copolymer fibers account for about 1.0% to about 5.0% by weight of the total weight of the heterogeneous material. The copolymer fibers shrink as a result of the introduction of heat to the heterogeneous material. The heat causes the holes originally in the scrim material or net to decrease in size and, thus, the heterogeneous material bunches or puckers as the copolymer shrinks, thereby forming the structure 40. Other means, for example microwaves, may be introduced to the heterogeneous material to cause the copolymer fibers to shrink. The structure 40 may be formed during the fabrication process or may be delayed until the product production process.

In accordance with one embodiment of this invention, the material may be creped before the initiation of differential shrinkage. Desirably, the material is a composite material or a heterogeneous material, as discussed above. Desirably, the material is a nonwoven spunbond web having a basis weight defined in terms of a base sheet basis weight, that is the basis weight of the nonwoven material prior to creping, and a creped basis weight, that is the basis weight of the nonwoven material after creping. Desirably, the base sheet basis weight of the material is about 0.2 osy to about 2.0 osy, more desirably about 0.3 osy to about 1.5 osy. To obtain the desired material and product performance, the base sheet basis weight is increased upon creping in the range of about 20% to about 150%, resulting in the creped material having a creped basis weight of about 0.24 osy to about 5.0 osy, more desirably about 0.36 osy to about 3.75 osy.

Figure 5:
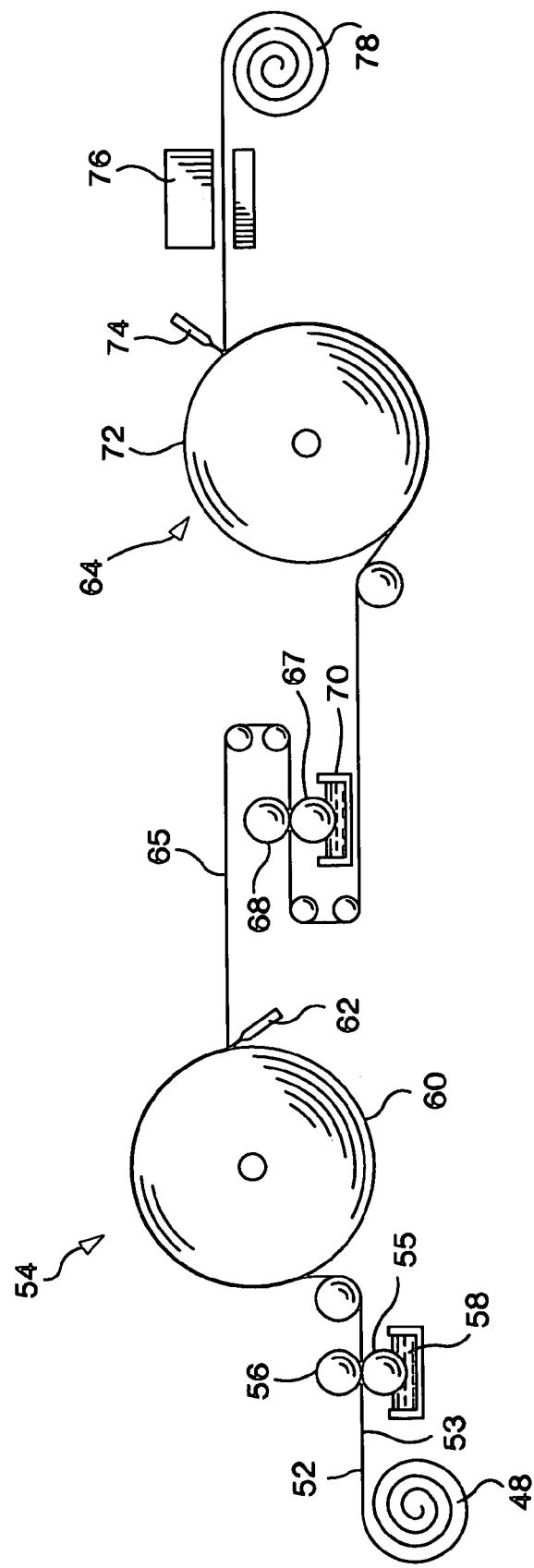
FIG. 5 is a schematic side view of an apparatus for creping a material in accordance with one embodiment of this invention.

As shown in FIG. 5, a nonwoven web 52 is unwound from a supply roll 48. The nonwoven web 52 is passed through a first creping station 54 and/or a second creping station 64. A first side 53 of the nonwoven web 52 may be creped using the first creping station 54. The first creping station 54 includes a first printing station including a lower patterned or smooth printing roller 55, an upper smooth anvil roller 56, and a printing bath 58, and also includes a dryer drum 60 and associated doctor or creping blade 62.

The rollers 55 and 56 nip the nonwoven web 52 and guide it forward. As the rollers 55 and 56 turn, the patterned or smooth printing roller 55 dips into the bath 58 containing an adhesive material, and applies the adhesive material to the first side 53 of the nonwoven web 52 in a partial coverage at a plurality of spaced apart locations, or in a total coverage. The adhesive-coated nonwoven web 52 is then passed around the dryer drum 60 whereupon the adhesive-coated surface 53 becomes adhered to the dryer drum 60. The first side 53 of the nonwoven web 52 is then creped (i.e. lifted off the drum and bent) using the creping blade 62.

A second side 65 of the nonwoven web 52 may be creped using the second creping station 64, the same or similar to the first creping station 54, regardless of whether the first creping station 54 has been bypassed. The second creping station 64 includes a second printing station including a lower patterned or smooth printing roller 67, an upper smooth anvil roller 68, and a printing bath 70, and also includes a dryer drum 72 and associated creping blade 74.

The rollers 67 and 68 nip the nonwoven web 52 and guide it forward. As the rollers 67 and 68 turn, the patterned or smooth printing roller 67 dips into the bath 70 containing an adhesive material, and applies the adhesive material to the second side 65 of the nonwoven web 52 in a partial coverage at a plurality of spaced apart locations, or in a total coverage. The adhesive-coated nonwoven web 52 is then passed around the dryer drum 72 whereupon the adhesive-coated surface 65 becomes adhered to the dryer drum 72. The second side 65 of the nonwoven web 52 is then creped (i.e. lifted off the drum and bent) using the creping blade 74.

After creping, the nonwoven web 52 may be passed through a chilling station 76 and wound onto a storage roll 78. The level of creping is affected by the surface speed of the storage roll 78 relative to the surface speed of the dryer drum 72. Desirably, the surface speed of the storage roll 78 is slower than the surface speed of the dryer drum 72. The level of creping is a measurement of creping and is calculated according to the following equation:

$$\text{Crepe level (\%)} = \frac{S_d - S_s}{S_d} \times 100;\qquad \text{Eq. (2)}$$

wherein $S_d$ is the surface speed of the dryer drum and $S_s$ is the surface speed of the storage roll. Desirably, the level of creping should generally be about 5–60%, more desirably about 15–45%, still more desirably about 20–30%. Alternatively, the creped nonwoven web 52 may be stabilized using the differential shrinkage process prior to winding the nonwoven web 52 onto the storage roll 78.

A wide variety of adhesive bonding materials may be utilized to reinforce the fibers of the nonwoven web 52 at the locations of adhesive application, and to temporarily adhere the nonwoven web 52 to the surface of the dryer drum 60 and/or 72. Elastomeric adhesives (i.e. materials capable of at least 75% elongation without rupture) are especially suitable. Suitable materials include without limitation aqueous-based styrene butadiene adhesives, neoprene, polyvinyl chloride, vinyl copolymers, polyamides, and ethylene vinyl terpolymers. The presently desired adhesive material is an acrylic polymer emulsion sold by the National Starch and Chemical Company under the trade name DUR-O-SET®. The adhesive may be applied using the printing technique described above, or may, alternatively, be applied by melt-blowing, melt spraying, dripping, splattering, or any other technique capable of forming a partial or total adhesive coverage on the thermoplastic nonwoven web 52.

The creping of the nonwoven web 52 is primarily manifested in the bonded areas of the base ("raw") nonwoven web 52, corresponding to the nonwoven web bond pattern. As a result of the creping, the bonded regions are bent out of plane so as to cause permanent creping of the nonwoven web 52, and the formation of filament looped regions in the unbonded regions alternating with (in between) the creped bonded regions.

The resulting creped nonwoven web 52 has low density, high permeability, excellent surface and bulk softness, recoverable stretch properties, surface topology, and permanent out-of-plane fiber orientation. In order to stabilize the creped nonwoven web, the nonwoven web 52 is heated to initiate the differential shrinkage of the different polymer components.

Figure 6:
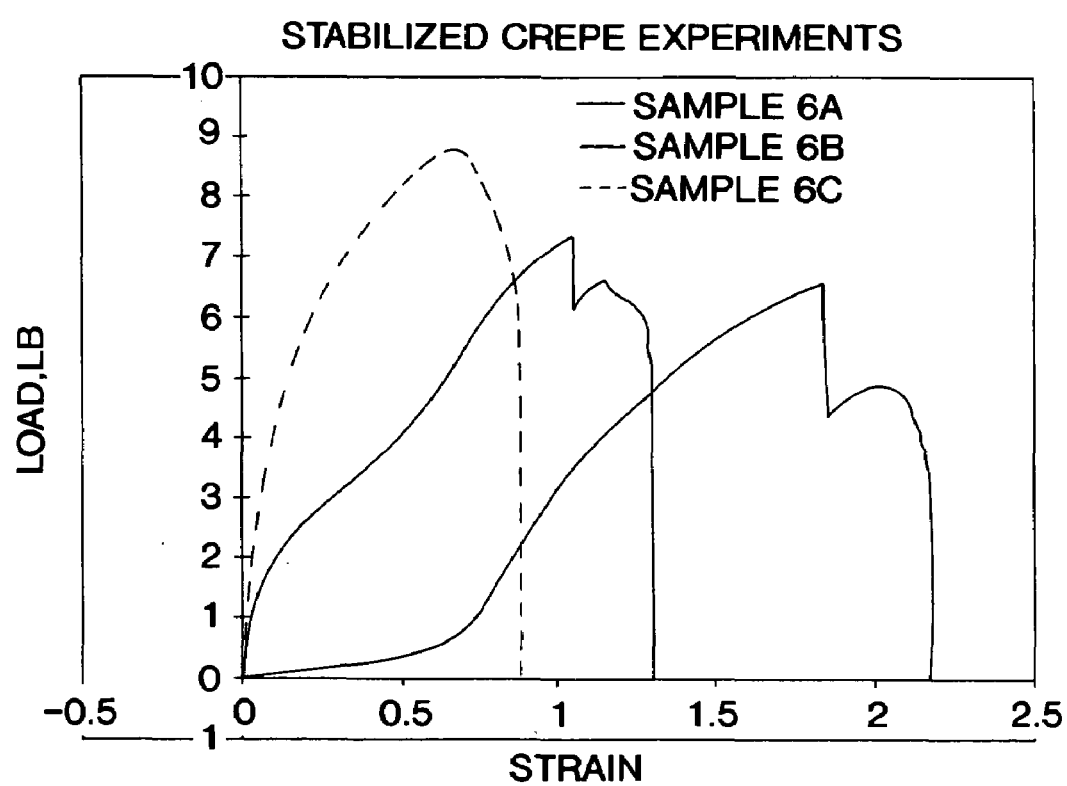
FIG. 6 is a stress-strain curve for a stabilized creped structured material produced in accordance with one embodiment of this invention.

Referring to FIG. 6, a bilayer spunbond web having a first layer of polypropylene polymer and a second layer of ethylene-polypropylene copolymer (3% by weight ethylene and 97% by weight propylene) was creped and then differentially shrunk using an infrared lamp. As indicated by the stress-strain curves, the structure 40 of the structured composite material 10 produced by the creping process was stabilized by the differential shrinkage process. The unstabilized creped material (sample 6A) has a very low resistance to pulling the crepe out of the material, as evident from the gradual slope of the stress-strain curve. The stabilized crepe (sample 6B) offers a greater resistance than the unstabilized crepe and the beginning of the respective stress-strain curve mimics the uncreped (sample 6C) curve where the strength of the material is being tested.

TEST METHODS

A. Rate Block Intake Test

Figure 7:
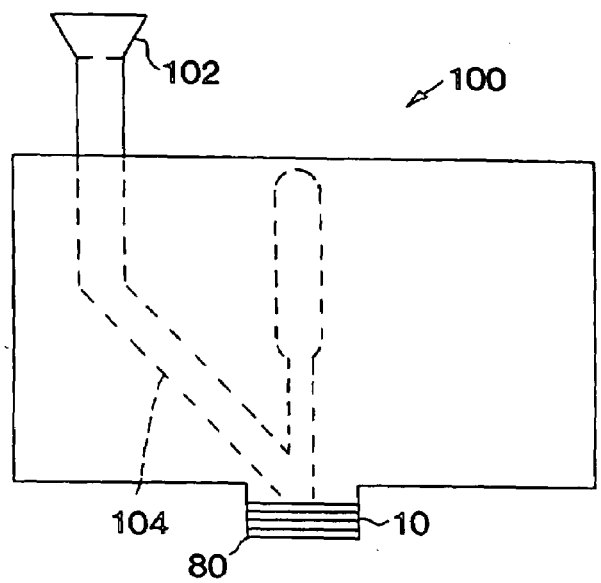
FIG. 7 is a schematic diagram of a rate block apparatus suitable for use in determining fluid intake time of a material or material system.

This test is used to determine the intake time of a known quantity of fluid into a material and/or material system. As shown in FIG. 7, the test apparatus consists of a rate block 100. A 4"×4" piece of absorbent 80 and structured material 10 are die cut. The specific structured materials 10 are described in the specific examples. The absorbent 80 used for these studies was standard and consisted of a 250 g/m² airlaid made of 90% Coosa 0054 and 10% HC T-255 binder. The total density for this system was 0.10 g/cc. The structured material 10 was placed over the absorbent 80 and the rate block 100 was placed on top of the two materials. 2 mL of a menses simulant was delivered into the test apparatus funnel 102 and a timer started. The fluid moved from the funnel 102 into a capillary 104 where it was delivered to the structured material 10 or material system. The timer was stopped when all the fluid was absorbed into the structured material 10 or material system as observed from the chamber in the test apparatus. The intake time for a known quantity of test fluid was recorded for a given structured material 10 or material system. This value is a measure of the structured material 10 or material system's absorbency. Typically, 5 to 10 repetitions of this test were performed and average intake time was determined.

B. Rewet Test

This test is used to determine the amount of fluid that will come back to the surface when a load is applied. The amount of fluid that comes back through the surface is called the "rewet" value. The more fluid that comes to the surface, the larger the "rewet" value. Lower rewet values are associated with a dryer material and hence a dryer product. In considering rewet, three properties are important: (1) intake, if the material/system does not have good intake then fluid can rewet, (2) ability of absorbent to hold fluid (the more the absorbent holds onto the fluid the less is available for rewet), and (3) flowback, the more the structured material 10 prohibits fluid from coming back through the structured material 10, the lower the rewet.

A 4"×4" piece of absorbent and structured material 10 were die cut. The specific structured materials 10 are described in the specific examples. The absorbent used for these studies was standard and consisted of a 250 g/m² airlaid made of 90% Coosa 0054 and 10% HC T-255 binder. The total density for this system was 0.10 g/cc. The structured material 10 was placed over the absorbent and the rate block was placed on top of the two materials. In this test, 2 mL of menses simulant are insulted into the rate block apparatus and allowed to absorb into a 4"×4" sample of the structured material 10 which is placed on top of the 4"×4" absorbent. The fluid is allowed to interact with the system for 1 minute and the rate block rests on top of the materials. The material system, structured material 10 and absorbent are placed onto a bag filled with fluid. A piece of blotter paper is weighed and placed on top of the material system. The bag is traversed vertically until it comes into contact with an acrylic plate above it, thus pressing the whole material system against the plate blotter paper side first. The system is pressed against the acrylic plate until a total of 1 psi is applied. The pressure is held fixed for 3 minutes after which the pressure is removed and the blotter paper is weighed. The blotter paper retains any fluid that was transferred to it from the material system. The difference in weight between the original blotter and the blotter after the experiment is known as the "rewet" value. Typically, 5 to 10 repetitions of this test were performed and average rewet was determined.

C. Pore Size Measurements

The pore radius distribution chart (FIG. 2) shows pore radius in microns in the x-axis and pore volume (volume absorbed in cc of liquid/gram of dry sample at that pore interval) in the y-axis. This is determined by using an apparatus based on the porous plate method first reported by Burgeni and Kapur in the *Textile Research Journal*, Volume 37, pp. 356–366 (1967). The system is a modified version of the porous plate method and consists of a movable Velmex stage interfaced with a programmable stepper motor and an electronic balance controlled by a computer. A control program automatically moves the stage to the desired height, collects data at a specified sampling rate until equilibrium is reached, and then moves to the next calculated height. Controllable parameters of the method include sampling rates, criteria for equilibrium and the number of absorption/desorption cycles.

Data for this analysis were collected using mineral oil in desorption mode. That is, the material was saturated at zero height and the porous plate (and the effective capillary tension on the sample) was progressively raised in discrete steps corresponding to the desired capillary radius. The amount of liquid pulled out from the sample was monitored. Readings at each height were taken every fifteen seconds and equilibrium was assumed to be reached when the average change of four consecutive readings was less than 0.005 g. This method is described in more detail in U.S. Pat. No. 5,679,042 by Eugenio Go Varona, incorporated herein by reference.

As shown in FIG. 2, samples 2a through 2d each were a bilayer spunbond web having a layer made of a polypropylene polymer with a Kaolin filler and a layer made of an ethylene-propylene random copolymer (3% by weight ethylene and 97% by weight propylene). Sample 2a was a control. Sample 2b was passed through a cure oven at a temperature of about 280° F. at a rate of about 250 feet per minute (fpm). Sample 2c was passed through the cure oven at a temperature of about 270° F. at a rate of about 70 fpm. Sample 2d was passed through the cure oven at a temperature of about 280° F. at a rate of about 70 fpm.

D. Basis Weight

The basis weight of a structured material is determined by measuring the mass of a structured material sample, and dividing it by the area covered by the sample.

E. Density

The density of a structured material is calculated by dividing the basis weight of a structured material sample by the thickness of the sample. For example, in Tables 2–5, the density of each sample was calculated using the following equation:

$$\text{Density} = (\text{basis weight, } osy \times 33.94)/(\text{bulk, } in \times 2.54). \qquad \text{Eq.(3)}$$

F. Air Permeability Test

This test determines the airflow rate through a specimen for a set area size and pressure. The higher the airflow rate per a given area and pressure, the more open the material is, thus allowing more fluid to pass therethrough. Air permeability was determined using a pressure of 125 Pa (0.5 inch water column) and was reported in cubic feet per minute per square foot. The air permeability data reported herein can be obtained using a TEXTEST FX 3300 air permeability tester.

G. Cup Crush Test

The softness of a nonwoven fabric may be measured according to the "cup crush" test. The cup crush test evaluates fabric stiffness by measuring the peak load or "cup crush" required for a 4.5 cm diameter hemispherically shaped foot to crush a 25 cm by 25 cm piece of fabric shaped into an approximately 6.5 cm diameter by 6.5 cm tall inverted cup while the cup shaped fabric is surrounded by an approximately 6.5 cm diameter cylinder to maintain a uniform deformation of the cup shaped fabric. An average of 10 readings is used. The foot and the cup are aligned to avoid contact between the cup walls and the foot which could affect the readings. The peak load is measured while the foot is descending at a rate of 40.6 cm/minute and is measured in grams. The cup crush test also yields a value for the total energy required to crush a sample (the "cup crush energy") which is the energy from the start of the test to the peak load point, i.e. the area under the curve formed by the load in grams on one axis and the distance the foot travels in millimeters on the other. Cup crush energy is therefore reported in g-mm. Lower cup crush values indicate a softer fabric. A suitable device for measuring cup crush is a Sintech Tensile Tester and 500 g load cell using TESTWORKS Software all of which are available from Sintech, Inc. of Research Triangle Park, N.C.

H. Tensile Test

This test measures the strip tensile/energy and elongation of a specimen. Samples are measured in the machine direction (MD) and the cross direction (CD). A sample of 3 inches×6 inches is placed on the pneumatic jaws of an Instron tensile tester with a load cell of 10 pounds, setting up the gage length to 3 inches and a crosshead speed of 12 inches/minute. The sample is placed on the clamps and the equipment is started. The top clamp is lifted by the equipment at the cross head speed until the specimen breaks. The strip tensile peak load (pounds), the maximum load before the specimen ruptures, and the elongation at break (%) (peak strain) are read from the instrument. The modulus is calculated in the typical manner as the slope of the best fitting line on a stress/strain curve as calculated from zero to the proportional limit. The energy is calculated with the following formula:

$$E = R/500 \times L \times S; \qquad \text{Eq. (4)}$$

where
E=Energy (inch per pound)
R=Integrator reading
L=Full scale load in pounds
S=Crosshead speed (inch/minute)

This is performed at a constant temperature of 73+/−2 F and a relative humidity of 50+/−2%.

EXAMPLE 1

A structured composite material 10 produced according to this invention having a first layer 20 made of a polypropylene polymer and a second layer 30 made of an ethylene-propylene copolymer 30 was tested for menses and rewet performance. The polypropylene polymer was made by the Exxon Mobil Chemical Company under the trade designation Exxon 3155 and the copolymer was made by Union Carbide under the trade designation 6D43. The structured composite material 10, as well as the other materials tested, were treated with 0.3% Ahcovel surfactant add-on. Ahcovel is made by Uniqema Inc., a division of ICI of New Castle, Del. The control code for the test was a standard polypropylene pad wrap produced commercially from Berkeley, 0.6 osy, EHP bond pattern, 0.3% Ahcovel treatment. The five codes were treated using a bench top dip and squeeze method.

Figure 8:
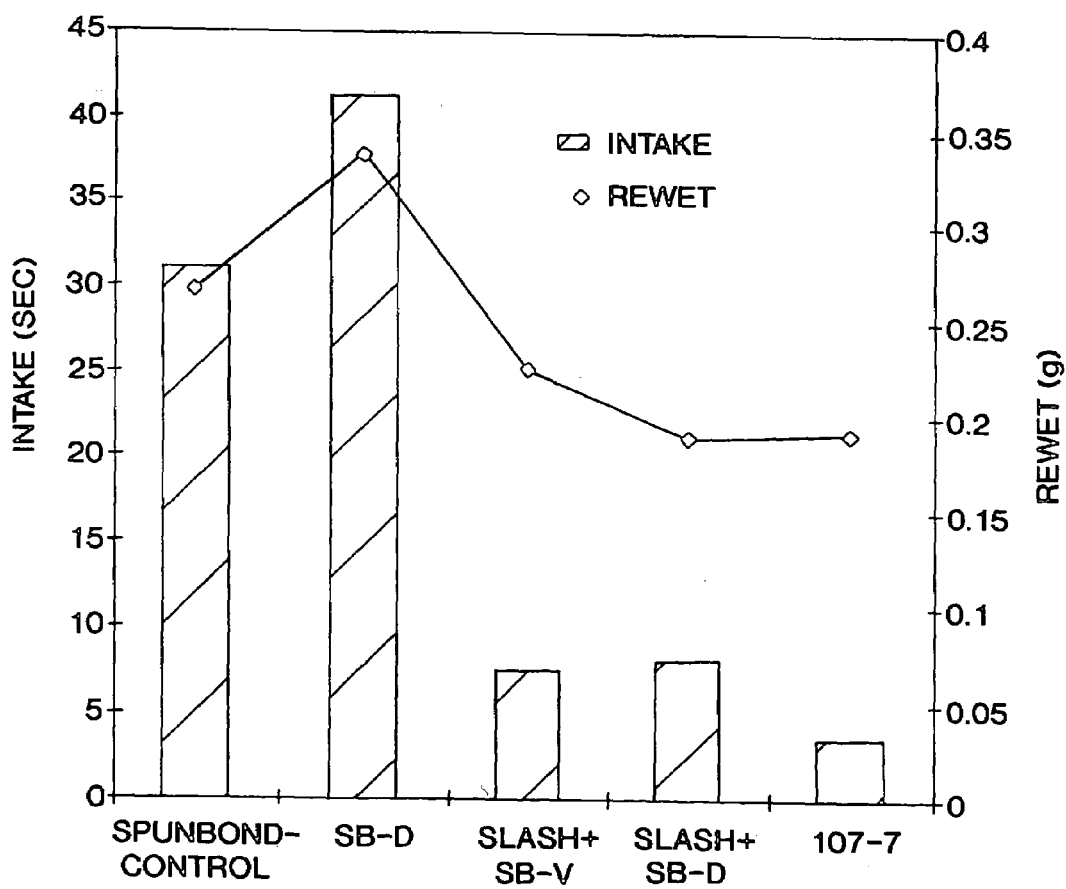
FIG. 8 is chart comparing the intake time and rewet value of a structured material produced in accordance with one embodiment of this invention with the intake time and rewet value of conventional cover materials.

As shown in FIG. 8, the structured composite material 10 (107-7 in FIG. 8) produced by differential shrinkage outperforms the other codes in terms of intake rate, less than 5.0 seconds, and rewet value, less than about 0.2 grams.

EXAMPLE 2

Polypropylene with 5% Kaolin/Ethylene-Propylene Copolymer

Five structured composite materials 10 were produced according to this invention having a first layer 20 made of a polypropylene polymer ("PP") with 5% Kaolin filler and a second layer 30 made of an ethylene-propylene copolymer ("CP") which contained 3% by weight ethylene and 97% by weight propylene. The polypropylene polymer was made by the Exxon Mobil Chemical Company under the trade designation Exxon 3155 and the copolymer was made by Union Carbide under the trade designation 6D43. Kaolin is a clay filler made by ECC located in Roswell, Ga. Each sample, except the control sample, was passed through a cure oven at a rate of about 50 fpm or about 250 fpm at a temperature of about 270° F. to about 290° F. The five samples were tested for bulk, basis weight, air permeability, cup crush energy, cup crush load and tensile strength. Table 2 shows the results of these tests.

TABLE 2

| Sample | Bulk (in) | Basis Weight (osy) | Basis Weight (g/m²) | Density (g/m²) | Air Perm. (cfm) | Cup Crush Energy (gm/mm) | Cup Crush Load (gm) |
|---|---|---|---|---|---|---|---|
| PP + Kaolin/CP Control | 0.016 | 0.70 | 24.90 | 0.058 | 1038 | 179 | 14 |
| PP + Kaolin/CP 250 fpm/280° F. | 0.033 | 1.10 | 33.80 | 0.045 | 879 | 310 | 22 |
| PP + Kaolin/CP 50 fpm/270° F. | 0.029 | 0.90 | 29.10 | 0.041 | 954 | 212 | 16 |
| PP + Kaolin/CP 50 fpm/280° F. | 0.066 | 1.80 | 59.50 | 0.036 | 769 | 1181 | 72 |
| PP + Kaolin/CP 50 fpm/290° F. | 0.060 | 1.80 | 59.70 | 0.040 | 794 | 1891 | 132 |

| Sample | Drape CD | Drape MD | Grab Peak Energy CD Dry (in-lb) | Grab Peak Energy MD Dry (in-lbs) | Grab Peak Load CD Dry (lbs) | Grab Peak Load MD Dry (lbs) | Grab Peak Strain CD Dry (%) | Grab Peak Strain MD Dry (%) |
|---|---|---|---|---|---|---|---|---|
| PP + Kaolin/CP Control | 1.83 | 1.83 | 24.6 | 19.9 | 5.6 | 5.3 | 238 | 192 |
| PP + Kaolin/CP 250 fpm/280° F. | 1.63 | 2.38 | 26.3 | 22.6 | 5.6 | 6.4 | 248 | 169 |
| PP + Kaolin/CP 50 fpm/270° F. | 1.25 | 2.28 | 27.1 | 20.3 | 5.3 | 5.4 | 270 | 193 |
| PP + Kaolin/CP 50 fpm/280° F. | 4.13 | 5.03 | 32.3 | 23.5 | 7.4 | 9.4 | 208 | 116 |
| PP + Kaolin/CP 50 fpm/290° F. | 5.80 | 6.10 | 13.7 | 18.6 | 8.5 | 12.9 | 91 | 73 |

EXAMPLE 3

Polypropylene/Ethylene-Propylene Copolymer

Five structured composite materials 10 were produced according to this invention having a first layer 20 made of the above polypropylene polymer and a second layer 30 made of the above ethylene-propylene copolymer. Each sample, except the control sample, was passed through a cure oven at a rate of about 50 fpm or about 250 fpm at a temperature of about 270° F. to about 290° F. The five samples were tested for bulk, basis weight, air permeability, cup crush energy, cup crush load and tensile strength. Table 3 shows the results of these tests.

TABLE 3

| Sample | Bulk (in) | Basis Weight (osy) | Basis Weight (g/m²) | Density (g/m²) | Air Perm. (cfm) | Cup Crush Energy (gm/mm) | Cup Crush Load (gm) |
|---|---|---|---|---|---|---|---|
| PP/CP Control | 0.016 | 0.70 | 23.30 | 0.058 | 1054 | 226 | 18 |
| PP/CP 250 fpm/280° F. | 0.057 | 1.10 | 38.10 | 0.026 | 815 | 736 | 56 |
| PP/CP 50 fpm/270° F. | 0.031 | 0.80 | 28.40 | 0.034 | 1006 | 199 | 16 |
| PP/CP 50 fpm/280° F. | 0.074 | 1.50 | 50.70 | 0.027 | 777 | 1299 | 106 |
| PP/CP 50 fpm/290° F. | 0.086 | 1.90 | 63.60 | 0.030 | 811 | 1959 | 143 |

| Sample | Drape CD | Drape MD | Grab Peak Energy CD Dry (in-lb) | Grab Peak Energy MD Dry (in-lbs) | Grab Peak Load CD Dry (lbs) | Grab Peak Load MD Dry (lbs) | Grab Peak Strain CD Dry (%) | Grab Peak Strain MD Dry (%) |
|---|---|---|---|---|---|---|---|---|
| PP/CP Control | 2.03 | 2.28 | 33.4 | 17.4 | 7.3 | 5.8 | 250 | 167 |
| PP/CP 250 fpm/280° F. | 2.90 | 3.23 | 30.6 | 21.3 | 8.2 | 8.2 | 207 | 134 |
| PP/CP 50 fpm/270° F. | 1.53 | 1.90 | 28.6 | 17.4 | 6.6 | 5.7 | 238 | 167 |
| PP/CP 50 fpm/280° F. | 4.20 | 3.90 | 35.0 | 24.7 | 9.7 | 11.8 | 188 | 103 |
| PP/CP 50 fpm/290° F. | 5.55 | 6.93 | 24.3 | 19.3 | 11.0 | 13.0 | 126 | 81 |

EXAMPLE 4

Polypropylene with 5% Kaolin (0.8 ghm)/Ethylene-Propylene Copolymer (0.5 ghm)

Five structured composite materials 10 were produced according to this invention having a first layer 20 made of the polypropylene polymer with 5% Kaolin filler and a second layer 30 made of the ethylene-propylene copolymer. The polypropylene polymer blend was extruded at 0.8 grams per hole per minute (ghm) and the ethylene-propylene copolymer was extruded at 0.5 ghm. Each sample, except the control sample, was passed through a cure oven at a rate of about 50 fpm or about 250 fpm at a temperature of about 270° F. to about 290° F. The five samples were tested for bulk, basis weight, air permeability, cup crush energy, cup crush load and tensile strength. Table 4 shows the results of these tests.

TABLE 4

| Sample | Bulk (in) | Basis Weight (osy) | Basis Weight (g/m²) | Density (g/m²) | Air Perm. (cfm) | Cup Crush Energy (gm/mm) | Cup Crush Load (gm) |
|---|---|---|---|---|---|---|---|
| PP + Kaolin/CP Control | 0.021 | 1.00 | 33.30 | 0.064 | 998 | 136 | 11 |
| PP + Kaolin/CP 250 fpm/280° F. | 0.035 | 1.20 | 42.00 | 0.046 | 837 | 270 | 21 |

TABLE 4-continued

| Sample | | | | | | | |
|---|---|---|---|---|---|---|---|
| PP + Kaolin/CP 50 fpm/270° F. | 0.030 | 1.10 | 37.10 | 0.049 | 972 | 154 | 13 |
| PP + Kaolin/CP 50 fpm/280° F. | 0.043 | 1.50 | 49.20 | 0.047 | 784 | 708 | 53 |
| PP + Kaolin/CP 50 fpm/290° F. | 0.067 | 2.20 | 74.50 | 0.044 | 737 | 1759 | 127 |

| Sample | Drape CD | Drape MD | Grab Peak Energy CD Dry (in-lb) | Grab Peak Energy MD Dry (in-lbs) | Grab Peak Load CD Dry (lbs) | Grab Peak Load MD Dry (lbs) | Grab Peak Strain CD Dry (%) | Grab Peak Strain MD Dry (%) |
|---|---|---|---|---|---|---|---|---|
| PP + Kaolin/CP Control | 1.40 | 1.93 | 16.9 | 9.3 | 4.0 | 3.8 | 228 | 131 |
| PP + Kaolin/CP 250 fpm/280° F. | 1.20 | 2.40 | 18.9 | 12.4 | 4.5 | 4.5 | 225 | 138 |
| PP + Kaolin/CP 50 fpm/270° F. | 1.25 | 1.58 | 14.8 | 8.5 | 3.3 | 3.2 | 231 | 140 |
| PP + Kaolin/CP 50 fpm/280° F. | 2.88 | 5.05 | 17.1 | 11.4 | 5.0 | 6.6 | 178 | 79 |
| PP + Kaolin/CP 50 fpm/290° F. | 4.68 | 5.45 | 19.7 | 14.7 | 8.1 | 10.7 | 125 | 67 |

EXAMPLE 5

Polypropylene with 5% Kaolin (0.5 ghm)/Ethylene-Propylene Copolymer (0.8 ghm)

Five structured composite materials 10 were produced according to this invention having a first layer 20 made of the polypropylene polymer with 5% Kaolin filler and a second layer 30 made of the ethylene-propylene copolymer. The polypropylene polymer blend was extruded at 0.5 grams per hole per minute (ghm) and the ethylene-propylene copolymer was extruded at 0.8 ghm. Each sample, except the control sample, was passed through a cure oven at a rate of about 50 fpm or about 250 fpm at a temperature of about 270° F. to about 290° F. The five samples were tested for bulk, basis weight, air permeability, cup crush energy, cup crush load and tensile strength. Table 5 shows the results of these tests.

TABLE 5

| Sample | Bulk (in) | Basis Weight (osy) | Basis Weight (g/m²) | Density (g/m²) | Air Perm. (cfm) | Cup Crush Energy (gm/mm) | Cup Crush Load (gm) |
|---|---|---|---|---|---|---|---|
| PP + Kaolin/CP Control | 0.020 | 0.95 | 32.30 | 0.063 | 938 | 164 | 13 |
| PP + Kaolin/CP 250 fpm/280° F. | 0.041 | 1.30 | 45.50 | 0.042 | 820 | 573 | 42 |
| PP + Kaolin/CP 50 fpm/270° F. | 0.053 | 1.40 | 48.20 | 0.035 | 847 | 367 | 31 |
| PP + Kaolin/CP 50 fpm/280° F. | 0.070 | 2.30 | 77.60 | 0.044 | 675 | 1846 | 127 |
| PP + Kaolin/CP 50 fpm/290° F. | 0.065 | 2.20 | 75.60 | 0.045 | 795 | 2275 | 214 |

| Sample | Drape CD | Drape MD | Grab Peak Energy CD Dry (in-lb) | Grab Peak Energy MD Dry (in-lbs) | Grab Peak Load CD Dry (lbs) | Grab Peak Load MD Dry (lbs) | Grab Peak Strain CD Dry (%) | Grab Peak Strain MD Dry (%) |
|---|---|---|---|---|---|---|---|---|
| PP + Kaolin/CP Control | 1.53 | 2.05 | 26.3 | 20.5 | 5.8 | 5.7 | 250 | 188 |
| PP + Kaolin/CP 250 fpm/280° F. | 1.55 | 2.43 | 31.6 | 25.3 | 6.7 | 7.8 | 258 | 156 |
| PP + Kaolin/CP 50 fpm/270° F. | 1.70 | 2.35 | 23.4 | 24.5 | 5.2 | 6.5 | 249 | 191 |
| PP + Kaolin/CP 50 fpm/280° F. | 4.80 | 5.63 | 32.4 | 30.4 | 8.7 | 11.0 | 187 | 122 |
| PP + Kaolin/CP 50 fpm/290° F. | 7.58 | 6.33 | 12.0 | 11.7 | 9.3 | 12.1 | 68 | 47 |

Although references made herein are directed to personal care absorbent products, it is apparent to one having ordinary skill in the art that the structured material 10 in accordance with this invention may be used for articles or products other than personal care absorbent products. Such articles or products include, but are not limited to, fabrics for conveying fluids, spacer layers, fasteners, filter medium for liquid and air filtration applications, and wipers. For example, fabrics that deliver a cream or a soap, wipers impregnated with cleaning agents, cleaning products which scrub and convey material away from the surface being cleaned, and other products that rely on porosity and topography to function. The structured material produced in accordance with this invention may also be used as a cost-effective replacement for materials such as surge materials, loop materials and outer covers.

While the invention has been described in detail with respect to specific embodiments thereof, it will be appreciated to those skilled in the art, upon attaining an understanding of the foregoing may readily conceive of alterations to, variations of and equivalents to these embodiments. Accordingly, the scope of the present invention should be assessed as that of the appended claims and any equivalents thereto.

What is claimed is:

1. A method for producing a structured composite material for accommodating passage of viscous fluids through the structured composite material, the method comprising the steps of:
   forming a first layer having a first shrinkage extent, the first layer comprising a nonwoven web;
   forming a second layer having a second shrinkage extent different from the first shrinkage extent, the second layer comprising a film and having openings through the second layer;
   bonding the second layer to the first layer to form a composite material; and
   shrinking the second layer relative to the first layer, thereby forming a plurality of fiber loop pores in the first layer and shrinking the openings through the second layer to form a plurality of pores smaller than the fiber loop pores.

2. The method of claim 1, wherein the first layer comprises a propylene polymer and the second layer comprises an ethylene-propylene copolymer.

3. The method of claim 1, further comprising the step of heating the composite material to effect shrinkage of the second layer.

4. The method of claim 1, wherein the second layer is bonded to the first layer by one of thermal bonding, pin bonding and differential speed bonding.

5. The method of claim 1, further comprising the step of stretching the second layer before the second layer is bonded to the first layer.

6. The method of claim 5, wherein the second layer is stretched in a machine direction to about 1.5 to about 6.0 times an initial length.

7. The method of claim 5, wherein the second layer is stretched in a machine direction to about 2.0 to about 4.0 times an initial length.

8. A method for producing a structured composite material for accommodating passage of viscous fluids through the structured composite material, the method comprising the steps of:
   forming a first layer having a first shrinkage extent;
   forming a second layer having a second shrinkage extent different from the first shrinkage extent, the second layer comprising a film and having openings through the second layer;
   bonding the second layer to the first layer to form a composite material;
   creping the composite material; and
   shrinking the second layer relative to the first layer, thereby forming a plurality of fiber loop pores in the first layer and shrinking the openings through the second layer to form a plurality of pores smaller than the fiber loop pores.

9. A method for producing a composite material having a structure for accommodating passage of viscous fluids through the composite material, the method comprising the steps of:
   forming a first layer having a first shrinkage extent, the first layer comprising a nonwoven web;
   applying a second layer to the first layer to form the composite material, the second layer comprising a film, having a second shrinkage extent different from the first shrinkage extent and having openings through the second layer; and
   heating the composite material to produce the structure, wherein the second layer shrinks relative to the first layer, thereby forming a plurality of fiber loop pores in the first layer and shrinking the openings through the second layer to form a plurality of pores smaller than the fiber loop pores.

10. A method for producing a composite material having a structure for accommodating passage of viscous fluids through the composite material, the method comprising the steps of:
    forming a first layer having a first shrinkage extent;
    creping the first layer;
    applying a second layer to the first layer to form the composite material, the second layer having a second shrinkage extent different from the first shrinkage extent and comprising a film and having openings through the second layer; and
    heating the composite material to produce the structure, wherein the second layer shrinks relative to the first layer, thereby forming a plurality of fiber loop pores in the first layer and shrinking the openings through the second layer to form a plurality of pores smaller than the fiber loop pores.

11. The method of claim 9, further comprising the step of stretching the second layer before the second layer is applied to the first layer.

12. The method of claim 9, further comprising the step of pattern embossing the first layer to form thermal bonds which extend through the first layer.

* * * * *